(12) United States Patent
Gasmi et al.

(10) Patent No.: US 7,837,668 B2
(45) Date of Patent: Nov. 23, 2010

(54) NEEDLE ASSEMBLY FOR USE IN DELIVERING PRECISE DOSAGES OF PROTEINACEOUS PHARMACEUTICAL COMPOSITIONS AND METHODS FOR USE OF SAME

(75) Inventors: Mehdi Gasmi, San Diego, CA (US); Elias T. Ketchum, La Mesa, CA (US); Dominick A. Vacante, San Diego, CA (US)

(73) Assignee: Ceregene, Inc., San Diego, CA (US)

( * ) Notice: Subject to any disclaimer, the term of this patent is extended or adjusted under 35 U.S.C. 154(b) by 137 days.

(21) Appl. No.: 11/545,609

(22) Filed: Oct. 10, 2006

(65) Prior Publication Data
US 2008/0086061 A1  Apr. 10, 2008

(51) Int. Cl.
*A61M 31/00* (2006.01)
*A61M 5/178* (2006.01)
*A61B 5/00* (2006.01)
(52) U.S. Cl. .............. 604/506; 600/585; 604/164.01
(58) Field of Classification Search .......... 604/158–163
See application file for complete search history.

(56) References Cited

U.S. PATENT DOCUMENTS

| 5,817,106 | A | 10/1998 | Real .................... 606/130 |
| 6,283,977 | B1 | 9/2001 | Ericsson et al. |
| 6,451,306 | B1 | 9/2002 | Tuszynski et al. |
| 6,683,058 | B1 | 1/2004 | Tuszynski |
| 6,851,431 | B2 | 2/2005 | Mayeri |
| 7,060,056 | B2 | 6/2006 | Palasis et al. |
| 7,071,172 | B2 * | 7/2006 | McCown et al. ........... 514/44 |
| 2005/0113767 | A1 | 5/2005 | Palasis et al. .............. 604/264 |
| 2005/0261234 | A1 | 11/2005 | Dorey et al. .............. 514/44 |
| 2006/0135945 | A1 * | 6/2006 | Bankiewicz et al. ....... 604/506 |

* cited by examiner

*Primary Examiner*—Kevin C Sirmons
*Assistant Examiner*—Imani Hayman
(74) *Attorney, Agent, or Firm*—DLA Piper LLP (US)

(57) ABSTRACT

The needle assembly of the invention is a quad-partite system for use with an arc-center stereotactic headframe that allows a clinician to deliver recombinant expression vectors through the needle assembly to targeted sites at exact depths in the brain. Methods for use of the needle assembly with a tube insert for the needle cannula that does not bind proteins, as in protein viral capsids, permit delivery of precise volumes of pharmaceutical compositions containing viral recombinant expression vectors for gene therapy.

6 Claims, 12 Drawing Sheets

NEEDLE ASSEMBLY FOR USE IN DELIVERING PRECISE DOSAGES OF PROTEINACEOUS PHARMACEUTICAL COMPOSITIONS AND METHODS FOR USE OF SAME

FIELD OF THE INVENTION

The invention relates to the field of devices for drug delivery to the central nervous system. More particularly, it relates to needle assemblies for use in stereotactic delivery of pharmaceutical compositions to the central nervous system. The invention further relates to methods for negating binding by materials contained in the needle assembly to peptides contained in the pharmaceutical composition.

BACKGROUND OF THE INVENTION

Gene therapy by delivery of transgenes encoding therapeutic neurotrophic factors into the brain offers great promise for treating neurodegenerative conditions such as Alzheimer's Disease, Parkinson's Disease and Huntington's Disease. The protocols by which these therapies are provided are highly exacting, requiring that the therapeutic composition dosage (e.g., viral titer) be consistently provided at precise locations in the brain, to ensure that a predictable amount of neurotrophic factor be delivered only to targeted cells.

For example, U.S. Pat. No. 6,451,306 provides a method for treating Alzheimer's Disease which requires donor cells containing a neurotrophic factor-encoding transgene to be grafted at pre-determined sites in the forebrain located no more than 5 mm apart and no more than 500 μm from a targeted cell. The dosage of donor cells provided at each site preferably falls within a range of 2 to 20 μl per ml of composition. Similarly, U.S. Pat. Nos. 6,683,058 and 6,851,431 provide methods to treat defects, disease or damaged cholinergic and dopaminergic neuron populations, respectively, by delivering transgenes at sites within 500 μm of a targeted neuron and no more than 10 mm apart. Such parameters leave the practicing neurosurgeon relatively little room for error in dosing or placement of each graft or transgene injection.

Yet the conventional drug delivery devices available for use in gene therapy of the brain do not necessarily provide the consistent precision the therapeutic protocols require. For example, it has been reported that polynucleotides can become inactivated when introduced through a conventional needle cannula; e.g., made of a metal such as stainless steel (see, e.g., U.S. Pat. No. 7,060,056). The '056 patent inventors opined that the metal interacted with polynucleotides in a way that compromised their pharmaceutical activity by inactivation, rather than binding (see, e.g., '056 patent, Example 10). However, the inventors have discovered that many commonly used viral recombinant expression vectors are not inactivated by contact with metals and the like, most likely due to their proteinaceous coating (e.g., the capsid proteins of a virus). Instead, such material retains its activity, but is lost during delivery to binding within the lumen of conventional metal needles. The extent of loss varies from passage to passage, which limits the clinician's ability to accurately predict how much viral vector will actually be delivered out of any given injection or infusion.

The margin for dosing error in gene therapy of the brain can be increased if the instruments utilized to deliver a neurotrophic factor-encoding transgene (e.g., as part of a viral vector) cannot be consistently and accurately targeted to cell populations that may be only microns apart. If a target cell is missed, the extent to which expressed neurotrophic factor secreted by another cell will diffuse to a targeted cell is limited. Therefore, improvements in therapeutic efficacy can be obtained by enhancing the accurate placement of transgene-containing donor cell grafts or viral vectors into the brain.

SUMMARY OF THE INVENTION

The invention provides a needle assembly for use in delivering viral vectors to the brain. The needle assembly of the invention is a quad-partite system for use with an arc-center stereotactic headframe that allows the clinician to deliver viral vectors through the needle assembly to targeted sites at depths in the brain with pinpoint precision.

The needle assembly is designed to be able to reach a predetermined depth into the brain tissue, which depth may be precisely and consistently adjusted through alterations in the position of headframe arc, to which the needle assembly is attachable. The needle assembly includes a drug delivery vessel, which is adapted to minimize or eliminate loss of pharmaceutical composition volume as the composition passes through the vessel into the targeted brain tissue. The assembly is particularly well-suited for use with proteinaceous pharmaceutical compostions, including capsid coated viral recombinant expression vectors.

BRIEF DESCRIPTION OF THE DRAWINGS

FIGS. 4A and 4B are side views of a needle cannula of the needle assembly of the invention, having a polymer tubing disposed therein. FIG. 4A shows the needle cannula with the tubing disposed therein, cut away along lines C-C and D-D to show the tubing and bore therethrough. FIG. 4B shows a modification of the cannula/tubing combination adapted for connection to a pump, cut away along lines C-C and D-D to show a first tubing and bore therethough, as well as along line E-E to show a second tubing and bore therethrough.

DETAILED DESCRIPTION OF THE INVENTION

The needle assembly of the invention includes four tubular elements, including three cannulae which each have a bore extending therethrough from a distal end to a proximal end, and a rigid stylet, or rod. The length of each tubular element is chosen so, when used together in the correct fashion, the element can be inserted into the brain tissue to an exact, pre-determined length. The needle assembly is removably attachable to the arc of an arc-center stereotactic headframe, and its targeting can be directed and refined by adjusting the position of the arc.

Figure 1:
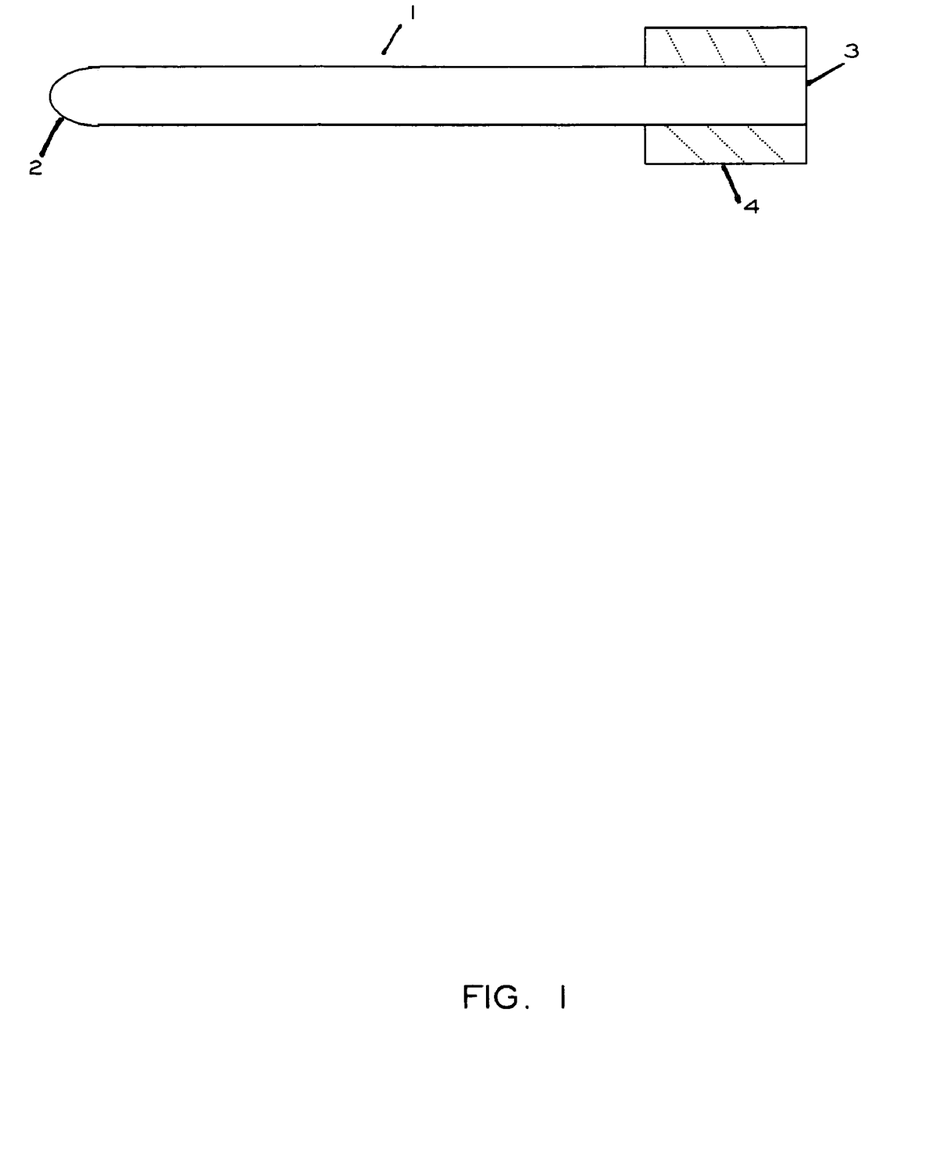
FIG. 1 is a side view of a stylet of the needle assembly of the invention.

Turning to FIG. 1, stylet 1 is shown in side view. Distal end 2 of stylet 1 is rounded to a smooth finish, and proximal end 3 is fitted with ferrule 4, which acts to stop forward progress of stylet 1 through a first cannula, as described further below, so distal end 2 protrudes therefrom to a pre-determined length. Stylet 1 is preferably a solid tube of a medically acceptable material, such as a metal (e.g., stainless steel), metal alloy (e.g., nitinol) or a polymer, most preferably a metal or metal alloy of sufficient strength and rigidity to press into or through the parenchyma under gentle pressure.

Figure 2:
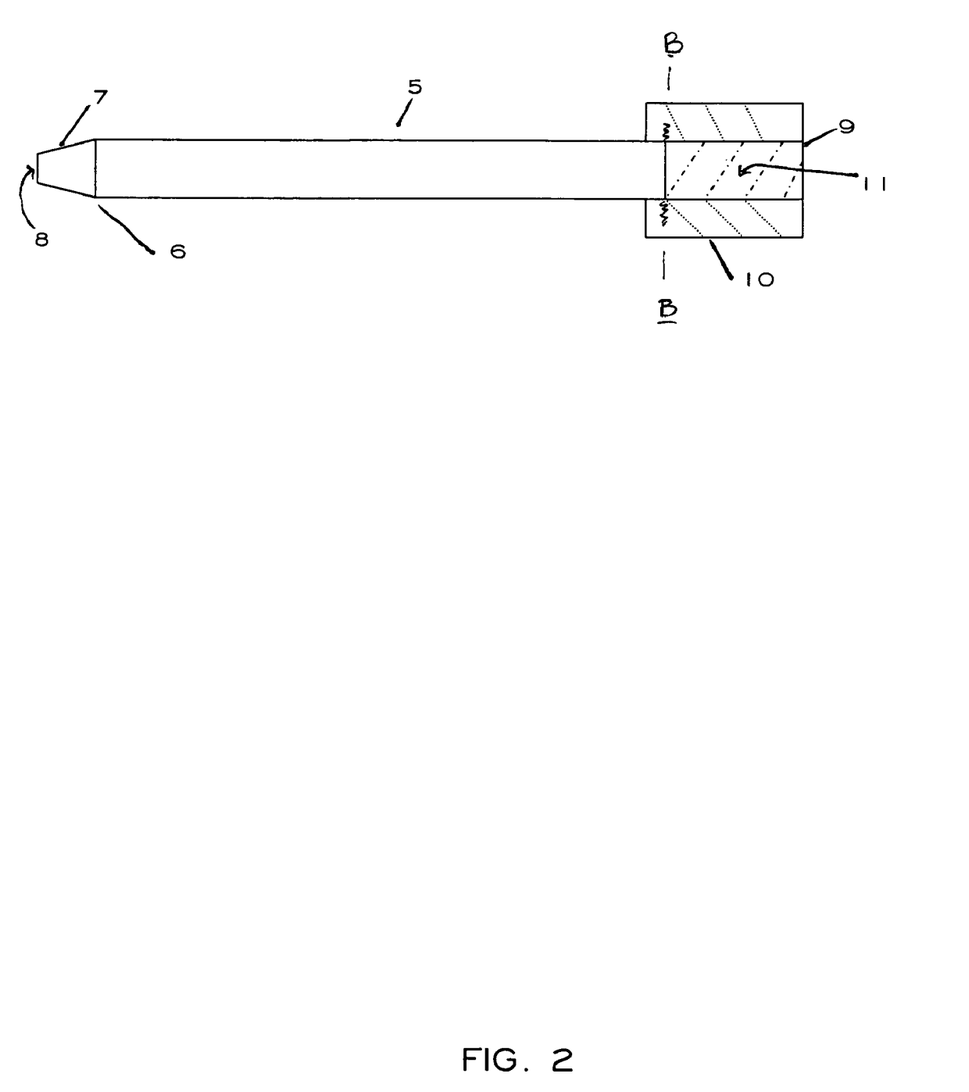
FIG. 2 is a side view of a needle guide of the needle assembly of the invention, cut away along line A-A to show the bore therethrough.

Stylet 1 is insertable with a close slidable fit through the bore of a first cannula 5 (FIG. 2), which serves as a needle guide during subsequent steps in the surgical protocol described herein. Distal end 6 of needle guide 5 consists of canted wall 7 ending at blunt tip 8. Both canted wall 7 and tip 8 have a smooth finish with no cutting edges. Proximal end 9 of needle guide 5 is fitted with ferrule 10, which acts to stop forward progress of needle guide 5 through a second cannula, as further described below, so distal end 6 protrudes therefrom to a pre-determined length. Needle guide 5 is provided with bore 11 therethrough from proximal end 9 through distal end 6. Bore 11 has an inner diameter slightly larger than the outer diameter of stylet 1, so the latter can be slidably inserted through the former with a contact fit.

Figure 3:
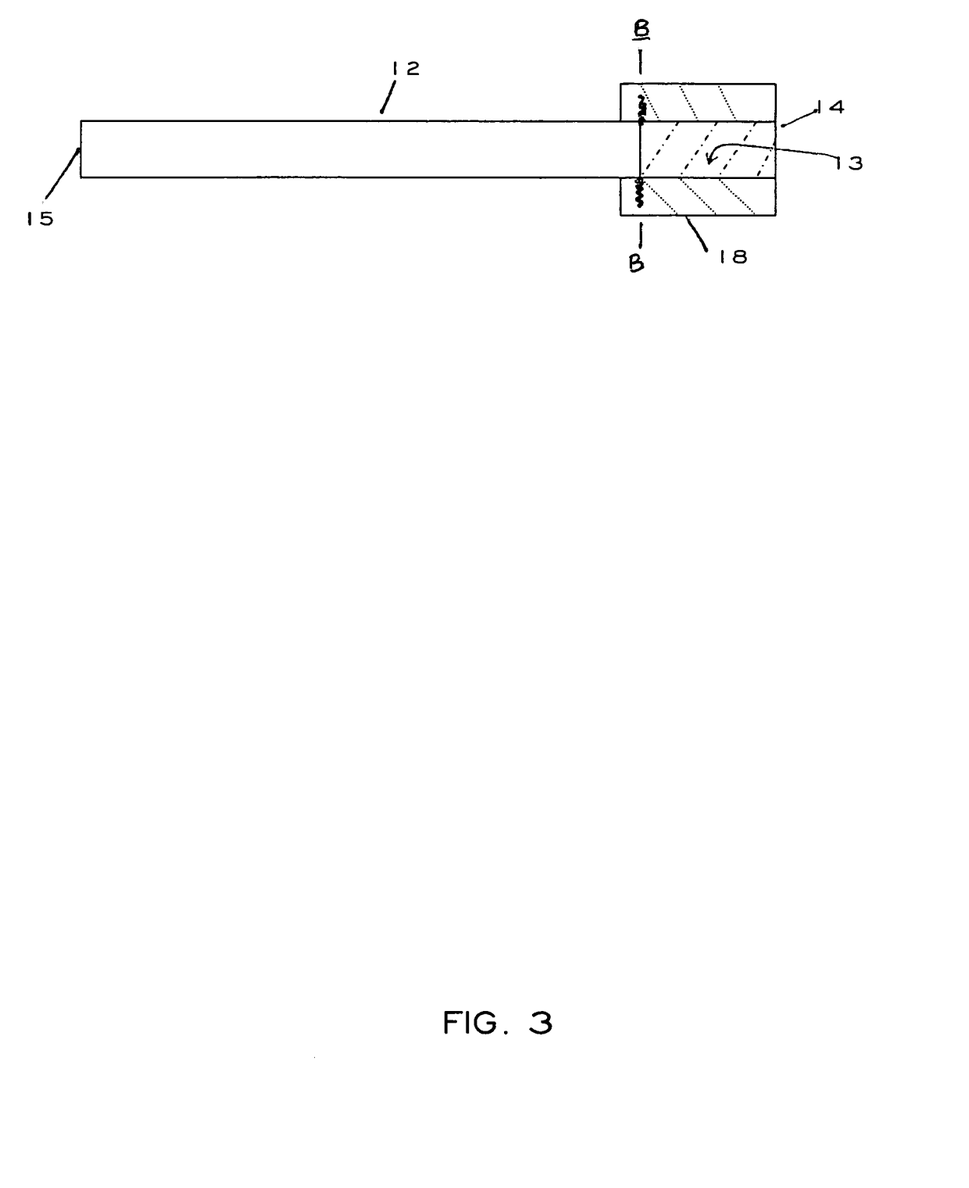
FIG. 3 is a side view of a guide tube of the needle assembly of the invention, cut away along line B-B to show the bore therethrough.
Figure 5:
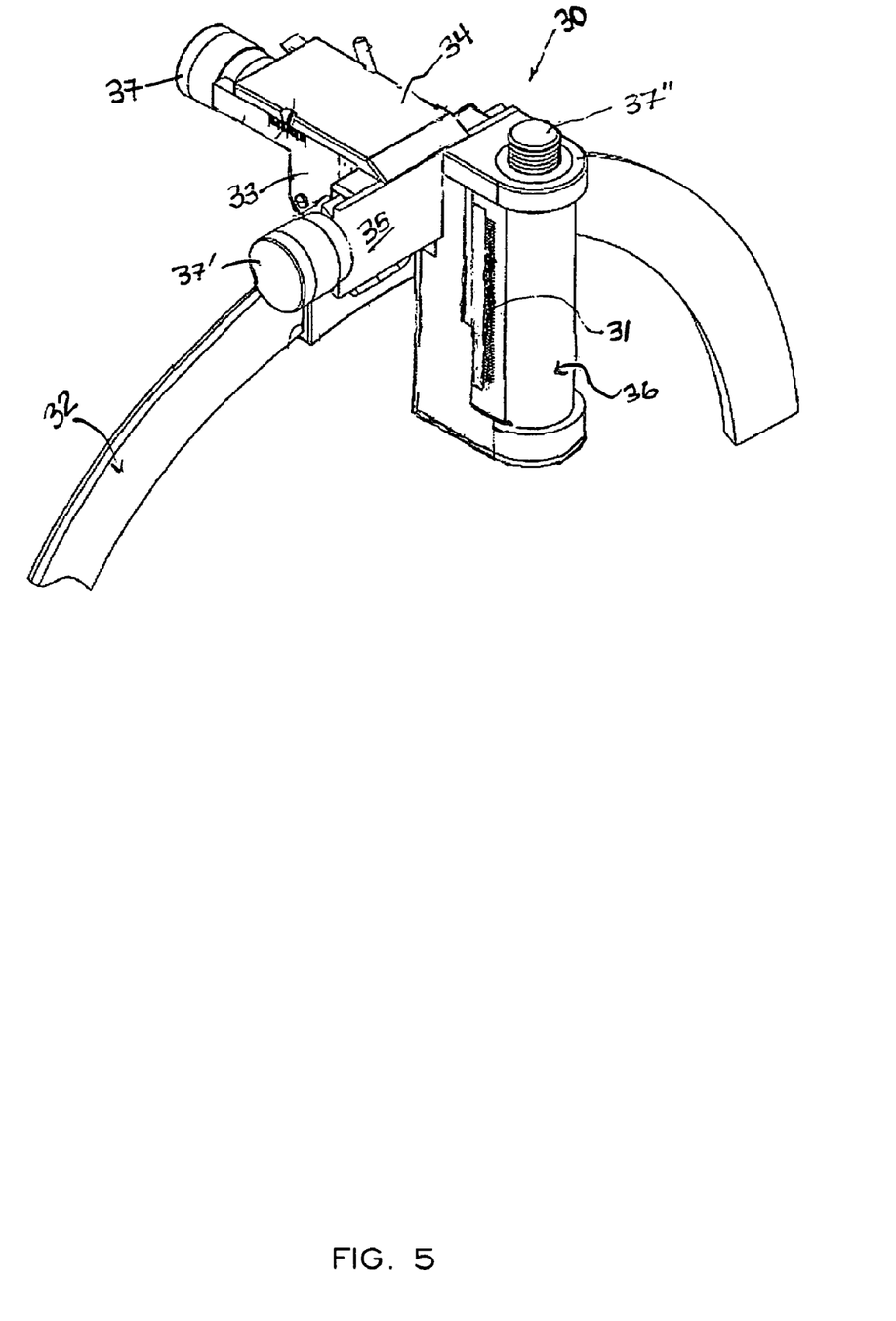
FIG. 5 depicts a stereotactic headframe of the arc-center Leksell type for use with the needle assembly of the invention.

As shown in FIG. 3, the second cannula serves as guide tube 12, which has bore 13 therethrough from its proximal end 14 to its distal end 15. Bore 13 has an inner diameter slightly larger than the outer diameter of needle guide 5, so the latter can be inserted through the former with a slidable contact fit. Distal end 15 of guide tube 12 consists of canted wall 16 ending at blunt tip 17. Both canted wall 16 and tip 17 have a smooth finish with no cutting edges. Proximal end 14 of guide tube 12 is fitted with attachment means, shown as ferrule 18, to attach guide tube 12 to the arc of an arc-center stereotactic headframe (as shown in FIG. 5). Depending on the design of the stereotactic headframe, attachment of guide tube 12 thereto may be indirect; e.g., by inserting guide tube 12 through an intermediary structure, such as a further guide tube (not shown) attached directly to the headframe.

Figure 4A:
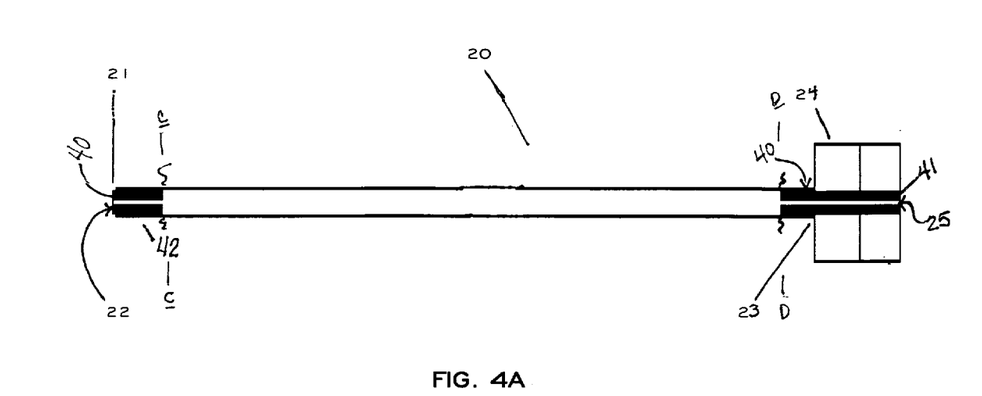
Figure 4B:
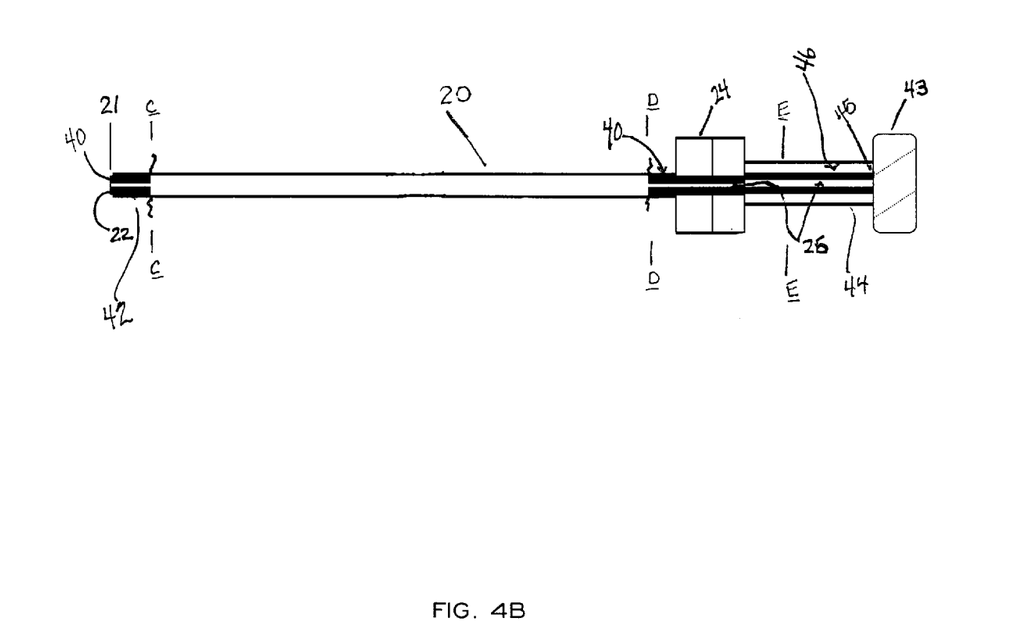

The third cannula is shown in FIGS. 4A and 4B, and serves as a drug delivery device. The preferred embodiment is depicted in FIG. 4A, wherein the drug delivery device is needle 20. Distal end 21 of needle 20 consists of tip 22. Tip 22 has a smooth finish with no cutting edges and may, if desired, be rounded to conform in geometry to tip 8 of needle guide 5. Proximal end 23 of needle 20 is fitted with ferrule 24, which acts to stop forward progress of needle 20 through needle guide 5, as described with respect to stylet 1, so distal end 21 protrudes therefrom to a pre-determined length. Needle 20 has an outer diameter slightly smaller than that of bore 11 through needle guide 5, so the former can be slidably inserted through the latter with a contact fit. Needle 20 has a bore 25 therethrough from proximal end 23 through distal end 21.

In use, guide tube 12 is attached to the stereotactic headframe and guided thereby to a pre-determined target site in the brain, which is exposed by an incision through the skull. Stylet 1 is placed through needle guide 5, which is then slidably inserted through guide tube 12 and placed under gentle pressure until forward progress of stylet 1 is stopped by contact between ferrule 4 and proximal end 14 of guide tube 12. As distal end 2 of stylet 1 protrudes beyond distal end 6 of needle guide 5, it bores into brain tissue to the target delivery site. Stylet 1 is removed once a path to the target site has been created by extending stylet 1 to its full length within needle guide 5.

Once stylet 1 is removed from needle guide 5, it is replaced by needle 20, whose full length of extension is the same or slightly less (by 9-10 mm) as stylet 1, with essentially the same outer diameter. Prior to insertion, bore 25 of needle 20 is pre-loaded with a pharmaceutical composition, preferably a proteinaceous composition, most preferably a composition comprising a viral recombinant expression vector having a proteinaceous capsid, which vector contains a neurotrophic factor-encoding transgene. The pharmaceutical composition is delivered into the target delivery site in the brain tissue by ejection from needle 20; e.g., by depressing the plunger of a syringe attached thereto at or proximal to ferrule 24, or initiating operation of a pump that controllably expels fluid out of needle 20.

To ensure precise placement of the needle assembly of the invention, guide tube 12 is attached by attachment means 18 to a stereotactic headframe 30, such as shown in FIG. 5. Headframes for use in neurosurgery are available commercially from a variety of sources, including the arc-center headframes whose use is preferred in the invention, such as the Leksell™ stereotactic system, the Cosman-Roberts-Wells™ headframe, and the Brown-Roberts-Wells™ headframe. The headframe of the Leksell system is as generally described in, for example, U.S. Pat. No. 6,283,977, and is depicted in FIG. 5. As shown in FIG. 5, the attachment means comprise coupling of the needle assembly to an instrument carrier 31 provided on arc 32 of headframe 30.

Briefly, the headframe is utilized on a patient as follows. A diagnostic procedure to map the location of the targeted treatment site is performed, such as computed tomography or magnetic resonance imaging. The image thereby obtained allows the neurosurgeon to compute the exact three-dimensional position of each target delivery site.

The entry site is selected, and both the entry site and intended target delivery site are mapped onto a "phantom," which relates each point to the patient's head. Coordinates are obtained from the phantom and entered into a computer which determines the final trajectory. Arc ring 32 is attached to support slide 33, in which the ring can slide in an arcuate recess (not shown). Support slide 33 includes means for perpendicular adjustment of arc ring 32's position, including an arc perpendicular slide 34. At the end of the latter, parallel adjusting means comprising an arc parallel slide 35. A microdrive casing 36 is attached to arc parallel slide 35, and instrument carrier 31 is attached to the casing. Adjustments are made (e.g., by turning of knobs 37, 37' and 37", which may be computer controlled). The needle assembly of the invention is attached to the headframe via attachment means (e.g., instrument carrier 31), and the needle inserted as described.

The needle assembly device of the invention in conjunction with a stereotactic headframe therefore ensures precise placement of a pharmaceutical composition into a delivery site in the brain, even when the site is at a depth beneath the surface.

However, when utilized according to the preferred embodiment of the invention to deliver a proteinaceous pharmaceutical composition, loss of composition from the intended dosage can still adversely impact the efficacy of treatment.

To mitigate such potential loss, the inner wall of bore 25 through needle 20 is adapted to prevent binding of the protein thereto. The invention is, in this aspect, particularly well suited for use with viral expression vectors that have little or no susceptibility to inactivation (loss of activity) but, due to proteinaceous components such as capsids, will bind to certain materials, especially metals and/or metal alloys.

It has been discovered that such binding, but not inactivation, is an issue for certain viral recombinant expression vectors in common usage for gene therapy, including adeno-associated virus (AAV) and lentivirus, but not for others, such as adenovirus.

For example, as demonstrated in Examples 8 and 9 below, a composition of AAV binds to stainless steel when passed through a stainless steel needle, but can be recovered by elution with NaCl. The effluent contains AAV that has the same level of infectivity as the virus initially loaded into the needle. Viral titers are also maintained in AAV and lentiviral compositions after passage through stainless steel cannulae and/or needle assemblies of the invention.

Figure 9:
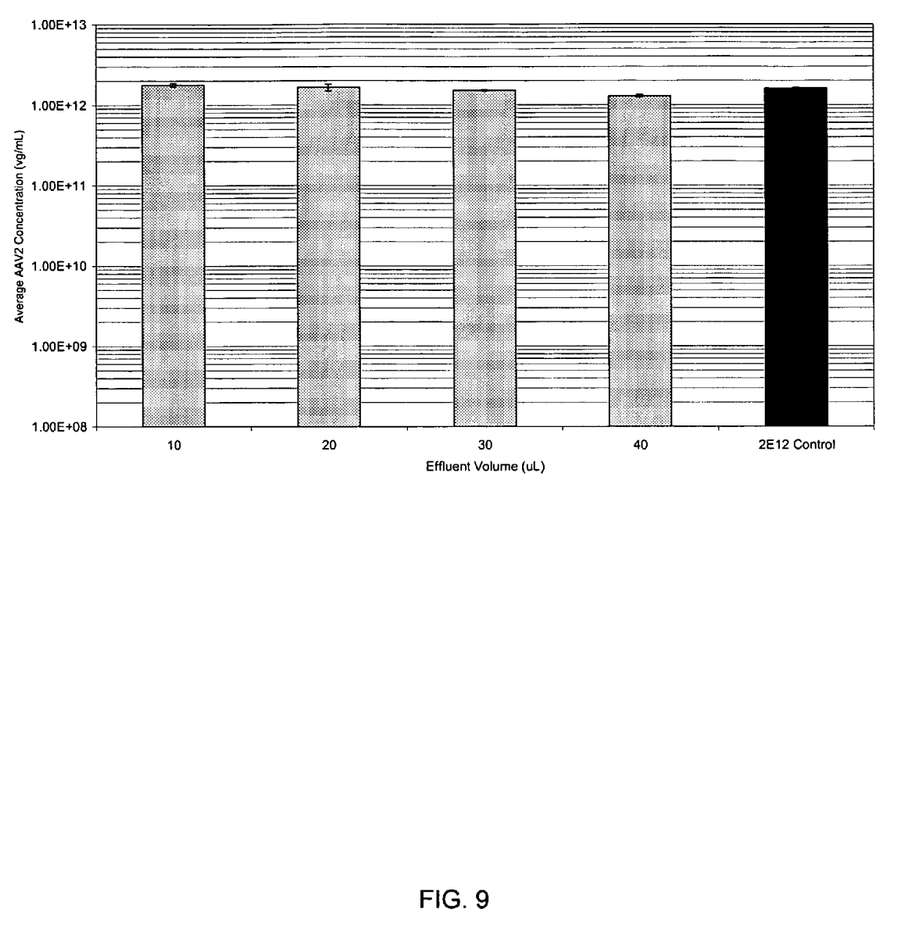
FIG. 9 is a graph demonstrating that AAV delivered through a stainless steel needle is not inactivated by contact with the metal.

However, compositions of AAV treated to remove all polynucleotide contamination of the viral capsid will bind to stainless steel, as shown in FIG. 9. The extent of binding dimishes after several passages of the viral composition through the metal cannula, indicating that the number of available binding sites decrease with repeated contact.

To minimize or eliminate such binding, a biocompatible polymer may be provided in the needle cannula, as shown in FIG. 4. The polymer is preferably a polycarbonate, polyether, polyamide, polyimide, polyethylene, polyurethane, polymerized halogenated ethylene, or derivatives thereof, most preferably a polyether block amide for its ease of manufacturing and superior performance in eliminating binding of capsid proteins. A suitable form of the latter for use in the invention is available commercially under the trademark Pebax® sold by, for example, Arkema, Inc.

Turning to FIG. 4A, disposed through bore 25 of needle 20 is a tube 40 composed entirely of Pebax®. Tube 40 has proximal end 41 and distal end 42. The latter is blunt and flattened at its tip 22, but may also be rounded, if desired, to conform to the geometry of tip 22 of needle 20. Preferably, tube 40 is essentially the same length as needle 20, but it may be shorter at either end by several millimeters without significantly compromising performance of the needle assembly of the invention in mitigating protein binding. Truncation of the end(s) of tube 40 might be chosen for ease of manufacturing if, for example, a uniform tube length was desired for use with needle cannulae of differing lengths.

Proximal end 41 of tube 40 protrudes from proximal end 23 of needle 20, terminating as ferrule 24. The latter serves as attachment means to secure needle 20 to a syringe, catheter or other vessel, such as a pump.

For example, as shown in FIG. 4B, needle 20 is adapted for connection to a fluid pump. Proximal end 23 of needle 20 terminates in ferrule 24. Tube 40 protrudes proximally beyond ferrule 24, terminating at proximal end 45 by connecting to a means for attachment (as shown, a female luer lock 43) to a pump (not shown). For stability, the proximally protruding portion of tube 40 is encircled by a second polymer tube 44 and disposed through bore 46 thereof. Preferably, second polymer tube 44 is somewhat less rigid than tube 40; e.g., the former may be formed of a different grade of Pebax® than the latter.

Preferably, tube 40 is securely attached within and to bore 25 of needle 20. For example, an adhesive attachment may be formed between tube 40 and bore 25 at the distal end 21 and proximal end 23 of needle 20. Conveniently, a biocompatible adhesive, such as Loctite® from Henkel Loctite Corporation, may be employed by injecting it between tube 40 and the inner wall of needle 20 at distal end 21 and proximal end 23 of the latter, from which sites the adhesive will travel by capillary action several millimeters before setting (at room temperature). Other biocompatible, low viscosity adhesives could also be employed.

The invention having been fully described, its practice is illustrated by the Examples below. The Examples shall not limit the scope of the invention, which is defined by the appended claims. However, in view of the teachings herein, equivalent designs and method steps for use in the invention may become apparent to those of ordinary skill in the art, all of which are to be considered part of the invention.

Example 1

AAV Titers are Conserved by Delivery with a Needle Assembly of the Invention Having a Polymeric Tube Disposed in a Metal Needle Pebax® and stainless steel needles (n=2 per needle type) attached to Hamilton syringes were loaded with AAV at an initial concentration of $2\times10^{12}$ vg/mL and used to deliver 4 consecutive 10 µL samples at a flow rate of 2 µL/min. The control sample represents a 10 µL aliquot of the AAV preparation that did not pass through any needle.

Figure 6:
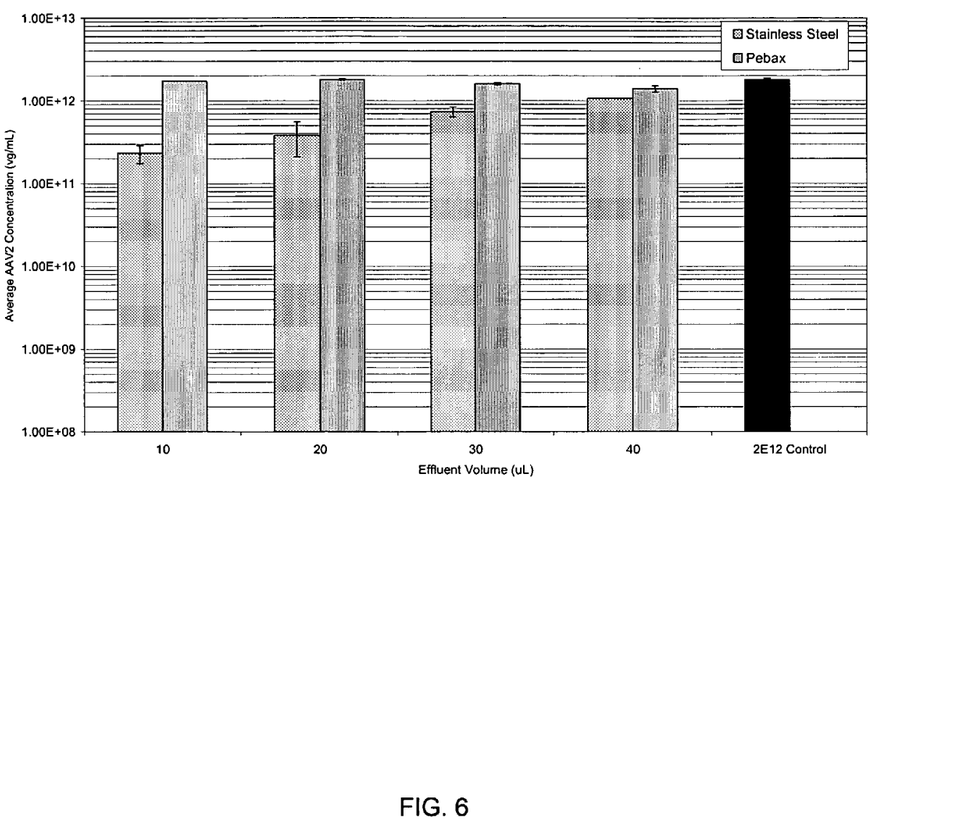
FIG. 6 is a graph demonstrating that AAV titers are conserved by delivery with a needle assembly of the invention having a polymeric tube disposed in a metal needle.

Analysis of DNase resistant particles by QPCR of the effluent samples revealed that AAV titer is conserved when delivered by Pebax® needles but not stainless steel needles (FIG. 6; error bars represent SEM).

Example 2

Figure 7:
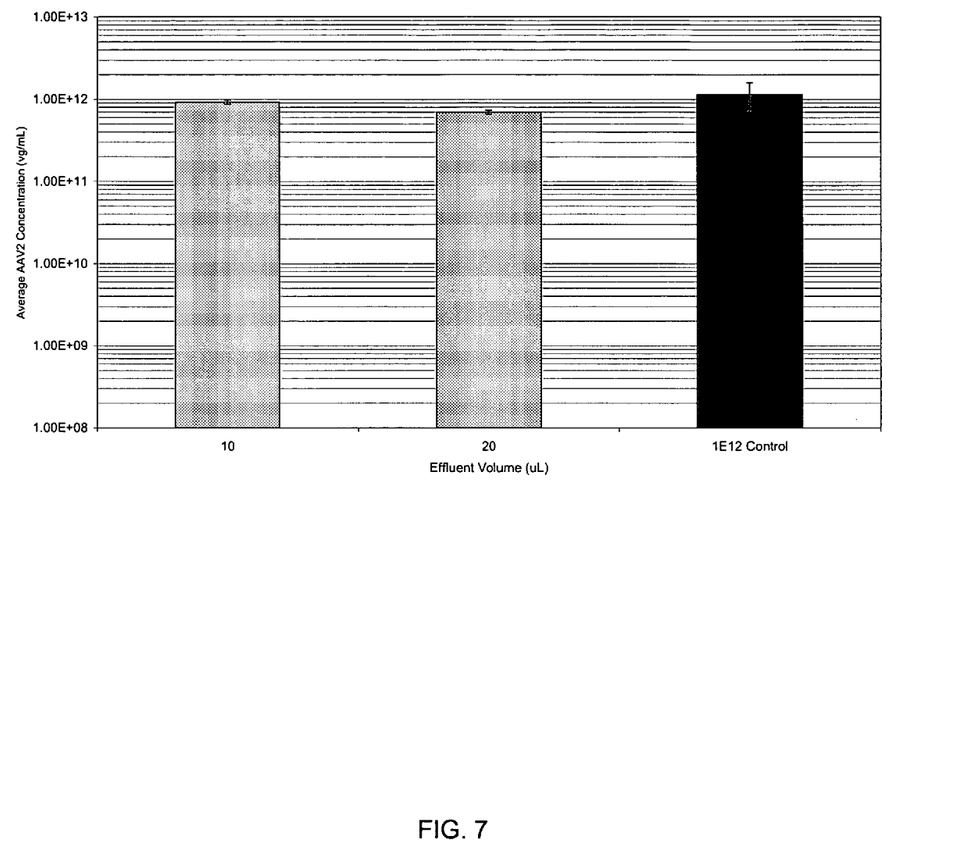
FIG. 7 is a graph that demonstrates that a needle assembly of the invention will deliver AAV without reduction at a 1 μL/min flow rate.

Needle Assemblies of the Invention Will Deliver AAV without Loss of Composition at a 1 µL/Min Flow Rate Pebax® needles (n=6) attached to Hamilton syringes were loaded with AAV at an initial concentration of $1\times10^{12}$ vg/mL and used to deliver 2 consecutive 10 µL samples at a flow rate of 1 µL/min. The control sample represents a 10 µL aliquot of the AAV preparation that did not pass through any needle (FIG. 7; error bars represent SEM).

Analysis of DNase resistant particles by QPCR of the effluent samples demonstrates that Pebax® needles deliver AAV at 1 µL/min without causing a reduction in titer.

Example 3

Figure 8:
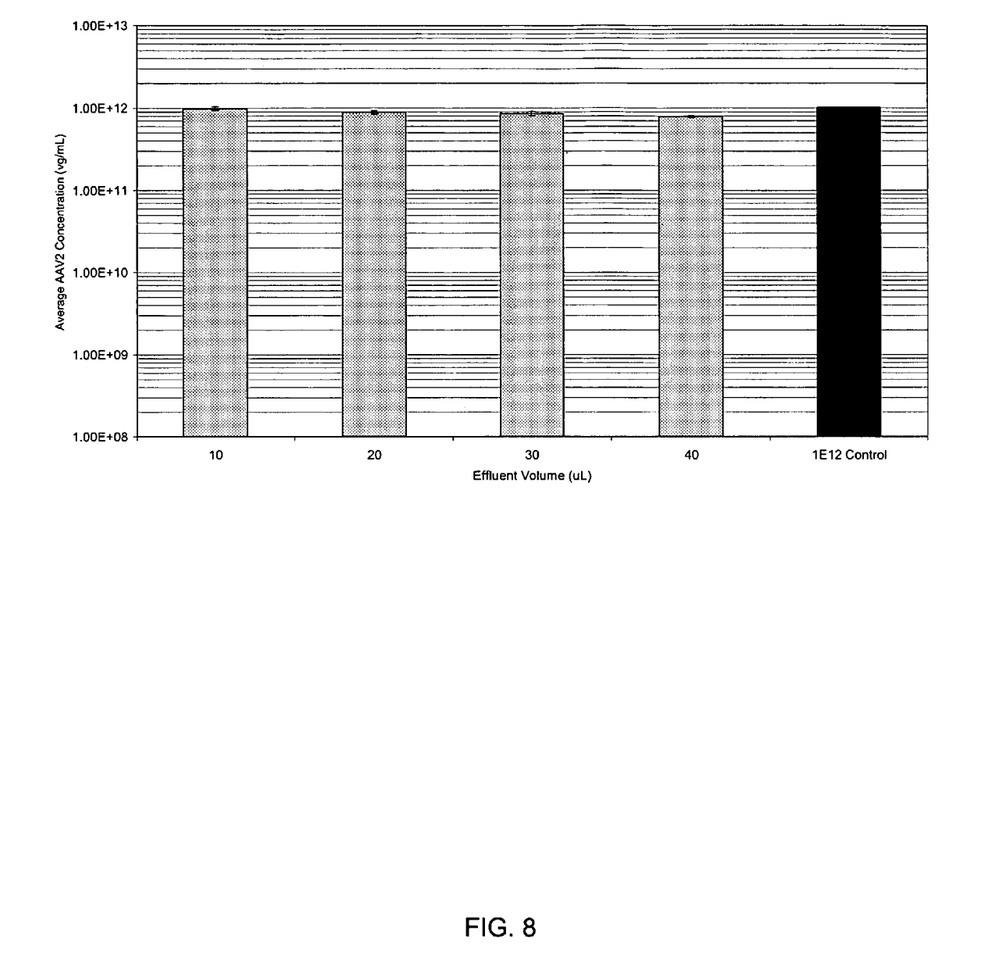
FIG. 8 is a graph that demonstrates that a needle assembly of the invention delivers a predictable dosage of AAV even after pre-loading of the viral composition.

Needle Assemblies of the Invention Deliver a Predictable Dosage of AAV Even after Pre-Loading of the Viral Composition Pebax® needles (n=3) attached to Hamilton syringes were loaded with AAV at an initial concentration of $1\times10^{12}$ vg/mL, held for 5 hours at room temperature, and then used to deliver 4 consecutive 10 µL samples at a flow rate of 2 µL/min. The control sample represents a 10 µL aliquot of the AAV preparation that did not pass through any needle (FIG. 8; error bars represent SEM).

Analysis of DNase resistant particles by QPCR of the effluent samples demonstrates that Pebax® needles deliver AAV without causing a reduction in titer even after being held loaded with AAV for 5 hours.

Example 4

AAV Delivered Through a Pebax® Tubing Retains its Bioactivity

Figure 10:
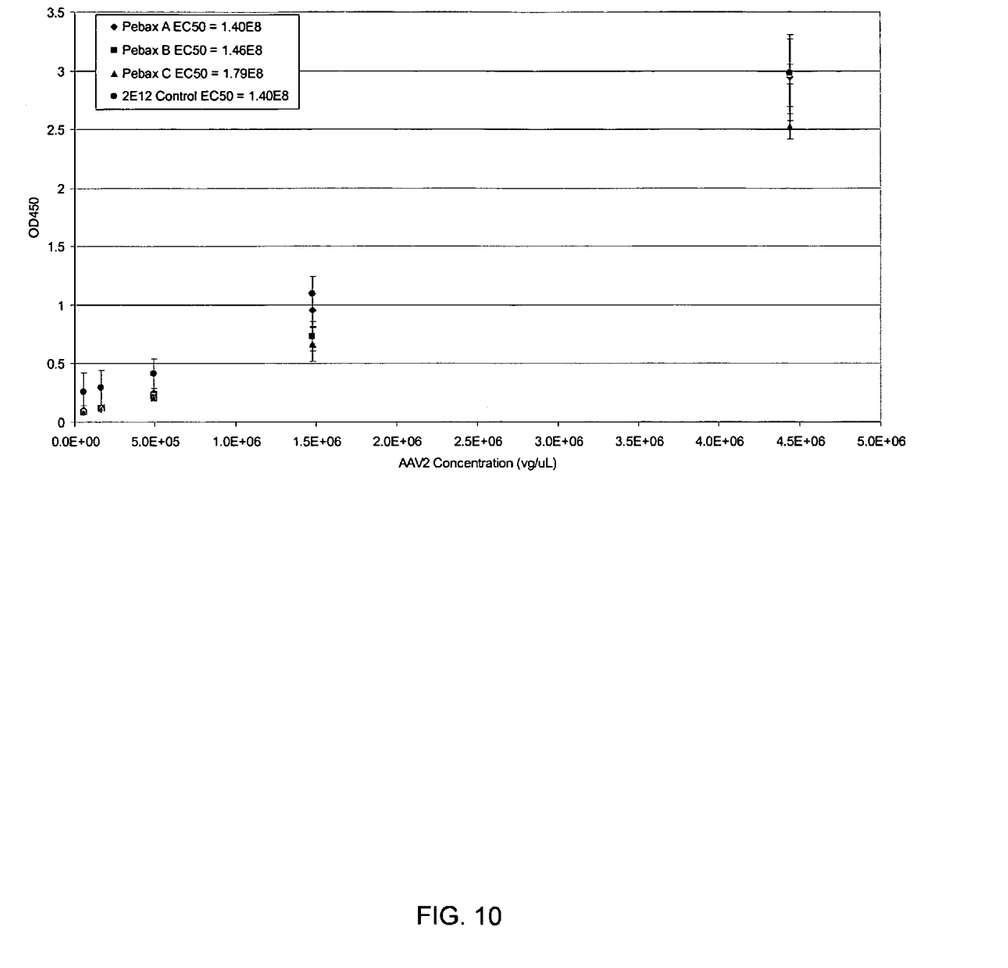
FIG. 10 is a graph demonstrating that AAV delivered through a Pebax® tubing retains its bioactivity.

Pebax® needles (n=3) were sterilized by gamma irradiation at 40.7-44.5 kGy, attached to Hamilton syringes, loaded with AAV at an initial concentration of $2 \times 10^{12}$ vg/mL, and used to deliver four consecutive 10 µL samples at a flow rate of 2 µL/min. 7 µL of the control sample and the first effluent sample (see FIG. 9) from each Pebax® needle (A-C) was used to transduce 293 cells. After 40 hours, supernatants were harvested from the cells and analyzed for the presence of neurturin protein by ELISA (FIG. 10; control bars represent SD).

These data show that the bioactivity of AAV is not compromised upon delivery with Pebax® needles.

Example 5

Figure 11:
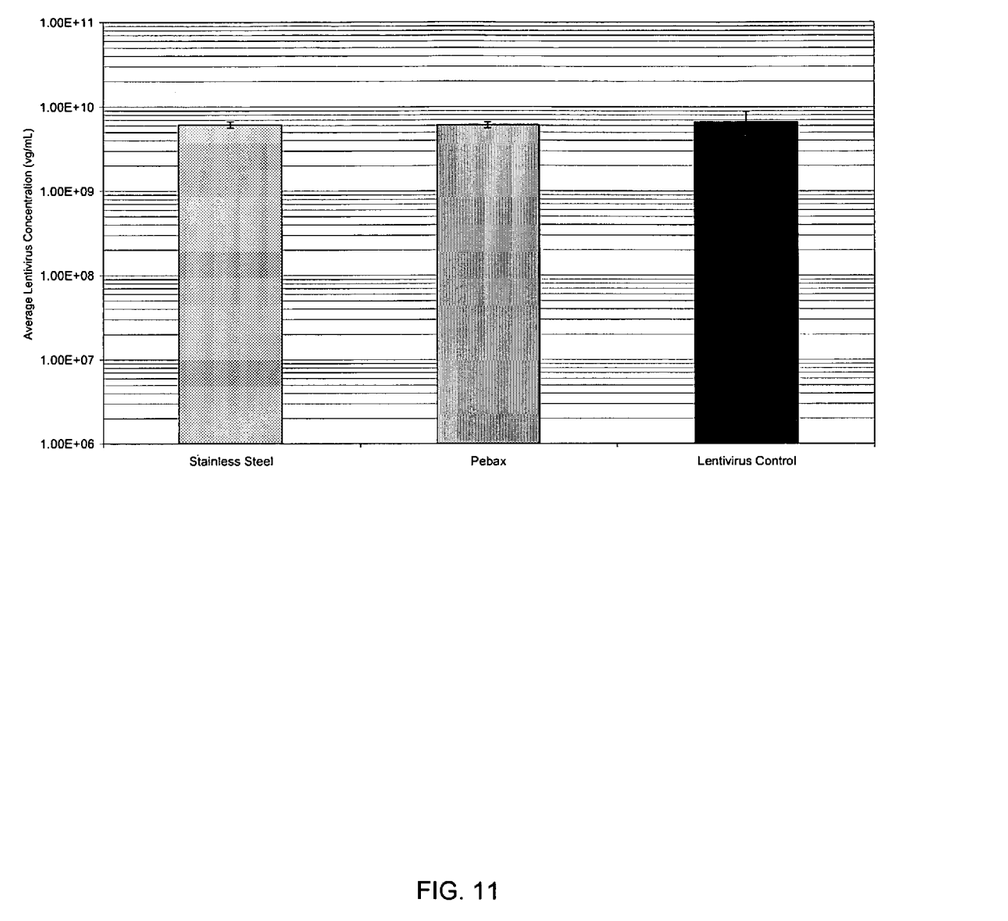
FIG. 11 is a graph demonstrating that lentivirus is not inactivated by contact with either a Pebax® or stainless steel needle.

Lentivirus is not Inactivated by Contact with Either a Pebax® or Stainless Steel Needle The needles (stainless steel or Pebax®, n=3 for each needle type) attached to Hamilton syringes were loaded with lentivirus at an initial concentration of $5 \times 10^9$ vg/mL and used to deliver one 15 µL sample at a flow rate of 1 µL/min. The control sample represents a 10 µL aliquot of the Lentivirus preparation that did not pass through any needle (FIG. 11; error bars represent SEM).

Analysis of DNase resistant particles by QPCR of the effluent sample demonstrates that Pebax® and stainless steel needles deliver another virus used in recombinant expression vectors, lentivirus, without causing a reduction in titer.

Example 6

Figure 12:
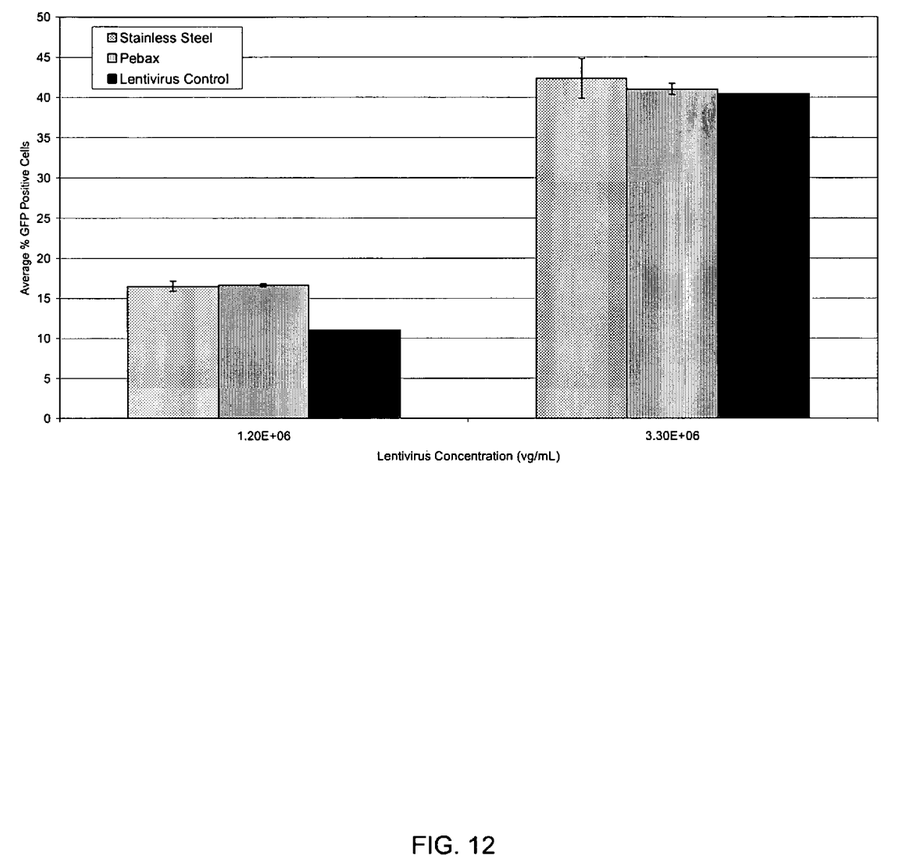
FIG. 12 is a graph demonstrating that the concentration of viral vector in an original dose of virus composition and in effulent obtained after passage of the composition through Pebax® and stainless steel needles is the same for the former, but not for the latter.

The Bioactivity of Lentivirus Vector in an Original Dose of Virus Composition Obtained after Passage of the Composition Through Pebax® and Stainless Steel Needles is the Same The needles (stainless steel or Pebax®, n=3 for each needle type) attached to Hamilton syringes were loaded with lentivirus at an initial concentration of $5 \times 10^9$ vg/mL and used to deliver one 15 µL sample at a flow rate of 1 µL/min. 10 µL of the control and effluent samples (see FIG. 11) from each needle type were used to transduce 293 cells. After 48 hours, cells were harvested and analyzed for the expression of green fluorescence protein (GFP) by Fluorescence Activated Cell Sorting (FACS) (FIG. 12; control bars represent SEM).

These data show that the bioactivity of lentivirus is not compromised upon delivery with Pebax® or stainless steel needles.

Example 7

Elution of AAV from Stainless Steel after Passage Therethrough of a Dosing Aliquot Demonstrates Binding of the Virus by the Metal 35 µL of AAV-GFP at an initial concentration of approximately $4 \times 10^{12}$ vg/mL was passed through stainless steel needles (n=4) at a flow rate of 1 µL/min and collected as effluent (35 µL). Needles were rinsed with 25 µL of formulation buffer 6 times to remove any residual AAV that was not strongly bound to the needles.

The needles were then loaded with 12 µL of 1M NaCl at 42° C. and held for 5 minutes at room temperature. The NaCl solution contained in the needles was collected after the 5-minute hold and the NaCl elution was repeated. Samples were analyzed by QPCR, which showed that an average of 55% ($6.75 \times 10^{10}$ vg) of the $1.5 \times 10^{11}$ vg exposed to the needles adsorbed to the needles and that an average of 50% of the needle bound AAV ($4.6 \times 10^{10}$ vg), or 30% of the total $1.5 \times 10^{11}$ vg exposed to the needles, was recovered from the needles through the 2 NaCl elutions performed.

The results of this experiment are summarized in the Table below.

TABLE 1

| Needle | Total vg Exposed | vg Recovered In Effluent | % of vg Rec in Effluent | Theoretical vg Bound | vg Recovered in NaCl Elution 1 | vg Recovered in NaCl Elution 2 | Total vg Rec in NaCl Elutions | % of vg Rec in NaCl Elutions | Effluent + NaCl | Total % Recovery |
|---|---|---|---|---|---|---|---|---|---|---|
| A | 1.50E+11 | 7.26E+10 | 48.42 | 7.74E+10 | 2.77E+10 | 9.05E+09 | 3.68E+10 | 24.50 | 1.09E+11 | 72.92 |
| B | 1.50E+11 | 6.56E+10 | 43.75 | 8.44E+10 | 3.80E+10 | 7.40E+09 | 4.54E+10 | 30.27 | 1.11E+11 | 74.02 |
| C | 1.50E+11 | 7.14E+10 | 47.60 | 7.86E+10 | 3.41E+10 | 9.25E+09 | 4.33E+10 | 28.87 | 1.15E+11 | 76.47 |
| D | 1.50E+11 | 6.00E+10 | 40.02 | 9.00E+10 | 4.83E+10 | 1.02E+10 | 5.84E+10 | 38.93 | 1.18E+11 | 78.95 |
| Average | 1.50E+11 | 6.74E+10 | 44.95 | 8.26E+10 | 3.70E+10 | 8.96E+09 | 4.60E+10 | 30.64 | 1.13E+11 | 75.59 |

Example 8

Elution of Bound AAV from Stainless Steel Demonstrates No Inactivation Thereof by the Metal AAV bound to stainless steel needles was eluted using 1M NaCl as described above in Example 7 (Table 1). 293 cells were transduced at an MOI of 3,333 (n=2 for control and n=8 for NaCl elutions) and 10,000 (n=2 for control and n=6 for NaCl elutions) using the NaCl elution samples and a control, which was not exposed to a stainless steel needle. The data in the Table below show that the infectivity of AAV that was bound to stainless steel needles is not reduced as compared to the control.

TABLE 2

| Sample | % GFP Positive Cells | SEM | Geo Mean Fluorescence | SEM |
|---|---|---|---|---|
| Negative Control | 0.04 | 0.02 | 30.64 | 0.32 |
| Control MOI 3333 | 16.75 | 0.06 | 62.87 | 0.03 |
| Control MOI 10000 | 35.39 | 0.67 | 75.32 | 0.57 |

TABLE 2-continued

| Sample | % GFP Positive Cells | SEM | Geo Mean Fluorescence | SEM |
|---|---|---|---|---|
| NaCl Elution MOI 3333 | 12.94 | 0.24 | 61.36 | 0.59 |
| NaCl Elution MOI 10000 | 30.78 | 0.78 | 73.62 | 0.94 |

The invention claimed is:

1. A method for delivering a precise volume of a proteinaceous pharmaceutical composition comprising an adeno-associated virus (AAV) or lentivirus recombinant expression vector having a polynucleotide-free protein capsid to a body tissue, the method comprising:
   (a) providing a drug delivery vessel, wherein substantially all portions thereof intended for contact with the pharmaceutical composition consist essentially of a biocompatible polymer that is essentially incapable of binding protein;
   (b) providing a known quantity of the pharmaceutical composition to the drug delivery vessel, wherein the protein capsid is capable of binding by adsorption to, but the vector is resistant to inactivation by, stainless steel; and,
   (c) causing the pharmaceutical composition to be expelled from the drug delivery vessel into the body tissue;
   wherein essentially all of the known quantity of the pharmaceutical composition provided is expelled into the body tissue, and
   wherein further, the drug delivery vessel is a needle assembly comprising:
   element (i), which is a stylet having a blunt distal end and a proximal end;
   element (ii), which is a needle guide having a rounded distal end, a proximal end, and a bore extending therethrough from said proximal end to said distal end, wherein said needle guide bore is slightly larger in inner diameter than the outer diameter of the stylet, so the latter is slidably insertable through the former;
   element (iii), which is a guide tube having a rounded distal end, a proximal end, and a bore extending therethrough from said proximal end to said distal end, wherein said guide tube bore is slightly larger in inner diameter than the outer diameter of the needle guide, so the latter is slidably insertable through the former, and wherein further the proximal end of the guide tube is fitted with means for attachment to a frame;
   element (iv), which is a needle cannula having a blunt distal end, a proximal end, and a bore extending therethrough from said proximal end to said distal end, wherein further said needle cannula is slightly smaller in outer diameter than the inner diameter of the needle guide, so the former is slidably insertable through the latter;
   wherein elements (i), (ii) and (iv) are each fitted with a stop at their proximal ends to prevent forward progress thereof through the bore of another element, and wherein further the length of elements (i), (ii) and (iv) of the needle assembly from their stops to their distal ends is such that the distal ends of element (i) or element (iv) protrude to a predetermined length from the distal end of element (ii) when inserted therethrough, and the distal end of element (ii) protrudes to a pre-determined length from the distal end of element (iii) when inserted therethrough.

2. The method according to claim 1, wherein the recombinant expression vector encodes a transgene.

3. The method according to claim 2, wherein the transgene expresses a neurotrophic factor.

4. The method according to claim 3, wherein the body tissue is the brain.

5. The method according to claim 1, wherein the needle assembly further comprises element (v) a drug delivery tube consisting of a polymer that is incapable of binding peptides contained in a proteinaceous pharmaceutical composition.

6. The method according to claim 1, wherein the polymer is a polyether block amide.

* * * * *